United States Patent
Ryu et al.

(10) Patent No.: US 11,123,192 B2
(45) Date of Patent: Sep. 21, 2021

(54) CERVICAL SPINE FIXATION APPARATUS

(71) Applicant: CG BIO CO., LTD., Gyeonggi-do (KR)

(72) Inventors: Hyun Seung Ryu, Gyeonggi-do (KR); Jun Hyuk Seo, Gyeonggi-do (KR); Byeong Woo Kwon, Gyeonggi-do (KR); Hae Jun Jeong, Gyeonggi-do (KR)

(73) Assignee: CG BIO CO., LTD., Gyeonggi-Do (KR)

( * ) Notice: Subject to any disclaimer, the term of this patent is extended or adjusted under 35 U.S.C. 154(b) by 48 days.

(21) Appl. No.: 15/767,974

(22) PCT Filed: Aug. 5, 2016

(86) PCT No.: PCT/KR2016/008638
§ 371 (c)(1),
(2) Date: Apr. 12, 2018

(87) PCT Pub. No.: WO2017/065400
PCT Pub. Date: Apr. 20, 2017

(65) Prior Publication Data
US 2018/0296348 A1 Oct. 18, 2018

(30) Foreign Application Priority Data
Oct. 13, 2015 (KR) .................. 10-2015-0142880
Oct. 13, 2015 (KR) .................. 10-2015-0142885

(51) Int. Cl.
*A61F 2/44* (2006.01)
*A61F 2/30* (2006.01)
(Continued)

(52) U.S. Cl.
CPC ........ *A61F 2/30749* (2013.01); *A61B 17/686* (2013.01); *A61B 17/70* (2013.01);
(Continued)

(58) Field of Classification Search
CPC ...... A61F 2/447; A61F 2/4465; A61F 2/4425; A61F 2/4611; A61F 2/4455;
(Continued)

(56) References Cited

U.S. PATENT DOCUMENTS 6,235,059 B1 * 5/2001 Benezech ............... A61F 2/447
623/17.16
7,172,627 B2 * 2/2007 Fiere ..................... A61F 2/4611
623/17.11
(Continued)

FOREIGN PATENT DOCUMENTS

JP 2013-169465 A 9/2013
KR 10-0513109 B1 1/2000
(Continued)

OTHER PUBLICATIONS

International Search Authority/KR, International Search Report dated Nov. 14, 2016 in International Patent Application No. PCT/KR2016/008638 (with English translation), 4 pages.
(Continued)

*Primary Examiner* — Zade Coley
(74) *Attorney, Agent, or Firm* — Masuvalley & Partners (57) ABSTRACT

The disclosure relates to a cervical spine fixation apparatus comprising: a body; a spacer; and a frame which is positioned on the lateral side of the spacer and couples with the spacer, wherein the frame has a coupling part for coupling with the body, and the body comprises a hole in which the coupling part of the frame is inserted. Or, the disclosure relates to a cervical spine fixation apparatus comprising: a body; and a spacer having a coupling part, wherein the body comprises a hole in which the coupling part is inserted, and the spacer moves with respect to the body.

14 Claims, 12 Drawing Sheets

(51) Int. Cl.
  *A61B 17/70* (2006.01)
  *A61B 17/86* (2006.01)
  *A61B 17/80* (2006.01)
  *A61B 17/68* (2006.01)

(52) U.S. Cl.
  CPC .......... *A61B 17/80* (2013.01); *A61B 17/8047* (2013.01); *A61B 17/86* (2013.01); *A61B 17/8685* (2013.01); *A61F 2/30771* (2013.01); *A61F 2/447* (2013.01); *A61F 2/4455* (2013.01); *A61F 2002/3082* (2013.01); *A61F 2002/30405* (2013.01); *A61F 2002/30476* (2013.01)

(58) Field of Classification Search
  CPC .... A61F 2/30749; A61F 2/30771; A61F 2/46; A61F 2002/3082; A61F 2002/30476; A61F 2002/30405; A61F 2/44–2002/4495; A61B 17/8033; A61B 17/8042; A61B 17/8645; A61B 17/8047; A61B 17/686; A61B 17/86; A61B 17/80; A61B 17/70
  See application file for complete search history.

(56) References Cited

U.S. PATENT DOCUMENTS

| | | | | |
|---|---|---|---|---|
| 7,850,731 | B2 * | 12/2010 | Brittan | A61F 2/4465 623/17.11 |
| 8,216,312 | B2 * | 7/2012 | Gray | A61F 2/4455 623/17.11 |
| 8,454,694 | B2 * | 6/2013 | Armstrong | A61F 2/30771 623/17.11 |
| 8,496,708 | B2 * | 7/2013 | Blain | A61F 2/447 623/17.16 |
| 8,932,358 | B1 * | 1/2015 | Nehls | A61F 2/4455 623/17.16 |
| 9,198,768 | B1 * | 12/2015 | Pisharodi | A61F 2/4425 |
| 9,364,341 | B2 * | 6/2016 | Gowan | A61F 2/4611 |
| 9,668,877 | B2 * | 6/2017 | Pavento | A61F 2/442 |
| 9,730,804 | B2 * | 8/2017 | Cowan, Jr. | A61F 2/447 |
| 10,159,517 | B2 * | 12/2018 | Leduc | A61B 17/8095 |
| 2001/0007941 | A1 * | 7/2001 | Steiner | A61B 17/8038 606/312 |
| 2005/0101960 | A1 * | 5/2005 | Fiere | A61F 2/4611 623/17.11 |
| 2005/0240267 | A1 * | 10/2005 | Randall | A61F 2/44 623/17.11 |
| 2006/0235533 | A1 * | 10/2006 | Blain | A61B 17/88 623/17.16 |
| 2009/0182430 | A1 * | 7/2009 | Tyber | A61F 2/4465 623/17.16 |
| 2009/0275988 | A1 | 11/2009 | Baynham | |
| 2010/0204737 | A1 | 8/2010 | Bae et al. | |
| 2010/0249937 | A1 * | 9/2010 | Blain | A61B 17/7059 623/17.16 |
| 2010/0312346 | A1 * | 12/2010 | Kueenzi | A61F 2/44 623/17.16 |
| 2012/0277868 | A1 | 11/2012 | Walters | |
| 2014/0058446 | A1 * | 2/2014 | Bernstein | A61F 2/4455 606/246 |
| 2015/0320569 | A1 * | 11/2015 | Pisharodi | A61F 2/4425 623/17.12 |

FOREIGN PATENT DOCUMENTS

| | | |
|---|---|---|
| KR | 10-2011-0011049 A | 2/2011 |
| KR | 10-2011-0033707 A | 3/2011 |
| WO | WO 2010/028045 A1 | 3/2010 |

OTHER PUBLICATIONS

European Patent Office, Supplementary European Search Report dated May 21, 2019 in European Patent Application No. 16858618. 1, 7 pages.

* cited by examiner

CERVICAL SPINE FIXATION APPARATUS

RELATED APPLICATIONS

This application is the U.S. National Phase of and claims priority to International Patent Application No. PCT/KR2016/008638, filed on Aug. 5, 2016, entitled "CERVICAL SPINE FIXATION APPARATUS" and claims priority under 35 U.S.C. § 119 to Korean Patent Application No. 10-2015-0142880, filed on Oct. 13, 2015 and Korean Patent Application No. 10-2015-0142885, filed on Oct. 13, 2015, both of which are hereby expressly incorporated by reference in their entirety for all purposes.

TECHNICAL FIELD

The disclosure relates to a cervical spine fixation apparatus, and more particularly, to a cervical spine fixation apparatus used with a spacer.

BACKGROUND ART

This section provides background information related to the disclosure which is not necessarily prior art.

Figure 1:
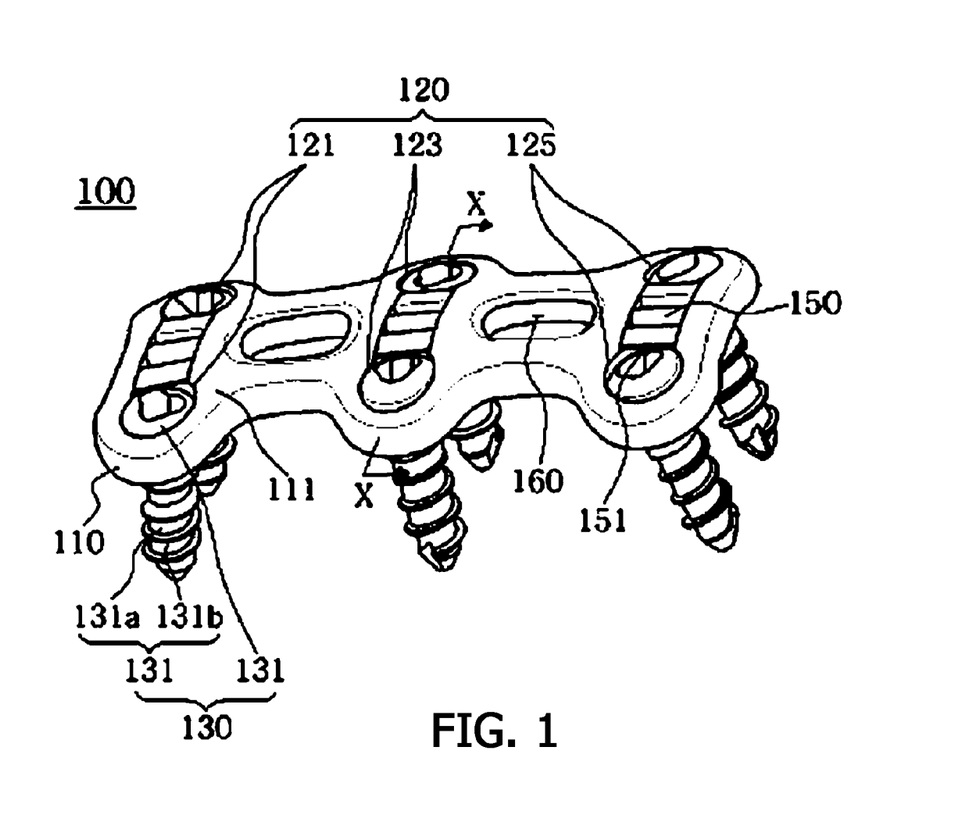
FIG. 1 is a view illustrating an example which is a cervical fixation apparatus disclosed in Korean Patent Registration Publication No. 10-0974498.

FIG. 1 is a view illustrating an example of a cervical spine fixation apparatus disclosed in Korean Patent Registration Publication No. 10-0974498, wherein a cervical spine fixation apparatus 100 is formed of a plate-shaped body 110. A body 110 includes a plurality of openings 120 (121, 123, and 125) formed therein, and screws 130 are inserted into the plurality of openings 120 (121, 123, and 125) and guided to be fixed to the bone. Meanwhile, the inserted screws 130 are prevented from being separated using an elastic cover 150. 151 refers to a separation prevention protrusion provided at the elastic cover 150, 160 refers to a window for checking an implant inserted in a cervical spine, 131 refers to a screw body, 131a refers to an outer circumferential surface, 131b refers to a screw thread, and 111 refers to a top side of the body, which are undescribed reference numerals.

Figure 2:
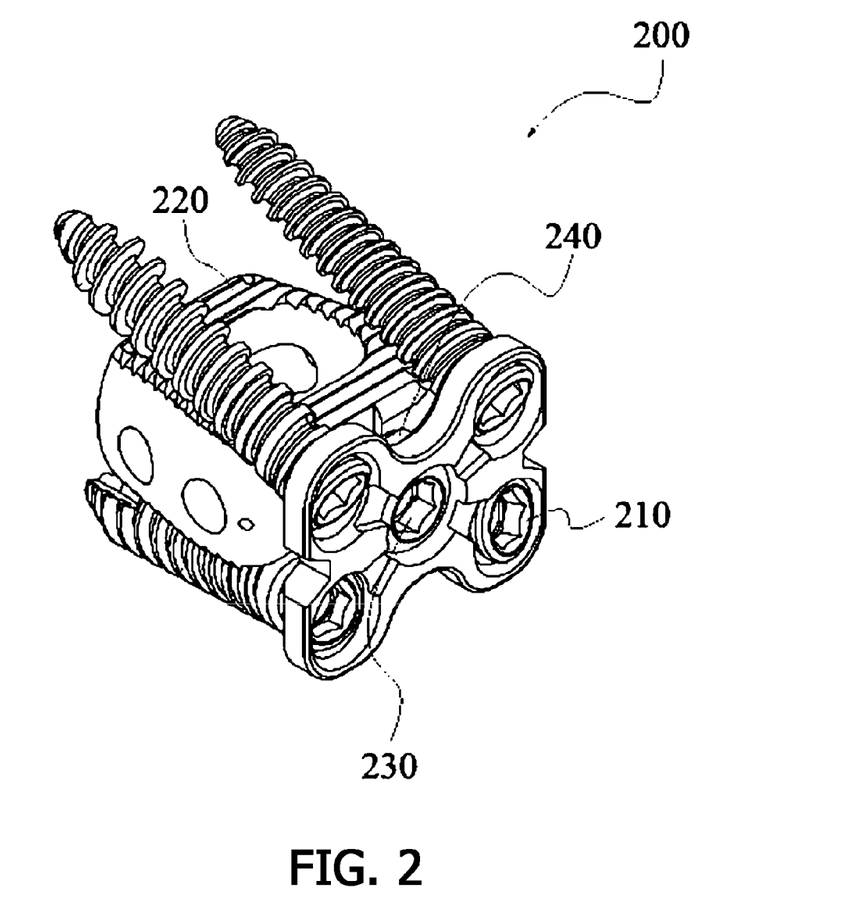
FIG. 2 is a view illustrating another example which is a cervical fixation apparatus disclosed in Korean Patent Laid-Open Publication No. 10-2011-0033707.

FIG. 2 is a view illustrating another example which is a cervical fixation apparatus disclosed in Korean Patent Laid-Open Publication No. 10-2011-0033707. For convenience of description, some reference numerals and names are changed.

A cervical spine fixation apparatus 200 includes a body 210 having a plate shape and a spacer 220 located between the body 210 and a cervical disk. The spacer 220 may be coupled to the body 210 by a fixing screw 230, and the spacer 220 may relatively move about the body 210 due to a movable washer 240. However, in the cervical spine fixation apparatus 200 shown in FIG. 2, it is necessary to form a screw hole (not shown) to be coupled to the fixing screw 230, in the spacer 220 to fix the spacer 220 to the body 210, and to use the movable washer 240, which is an additional component, to allow the spacer 220 to relatively move about the body 210, which is inconvenient.

The disclosure is directed to providing a cervical spine fixation apparatus which facilitates coupling between a spacer and a body and does not need to use additional components for allowing the spacer to relatively move about the body.

DISCLOSURE OF INVENTION

Technical Problem

The technical problem will be described at a latter part of "Mode for Invention."

Technical Solution

This section provides a general summary of the disclosure and is not a comprehensive disclosure of its full scope or all of its features.

According to one aspect of the disclosure, there is provided a cervical spine fixation apparatus including a body, a spacer, and a frame which is located on a lateral side of the spacer and coupled to the spacer and includes a coupling portion coupled to the body, in which the body includes a hole into which the coupling portion of the frame is inserted.

According to another aspect of the disclosure, there is provided a cervical spine fixation apparatus including a body and a spacer including a coupling portion, in which the body includes a hole into which the coupling portion is inserted, and the spacer moves about the body.

Advantageous Effects

The advantageous effects will be described at a latter part of "Mode for Invention."

MODE FOR INVENTION

Hereinafter, the disclosure will now be described in detail with reference to the accompanying drawings.

Figure 3:
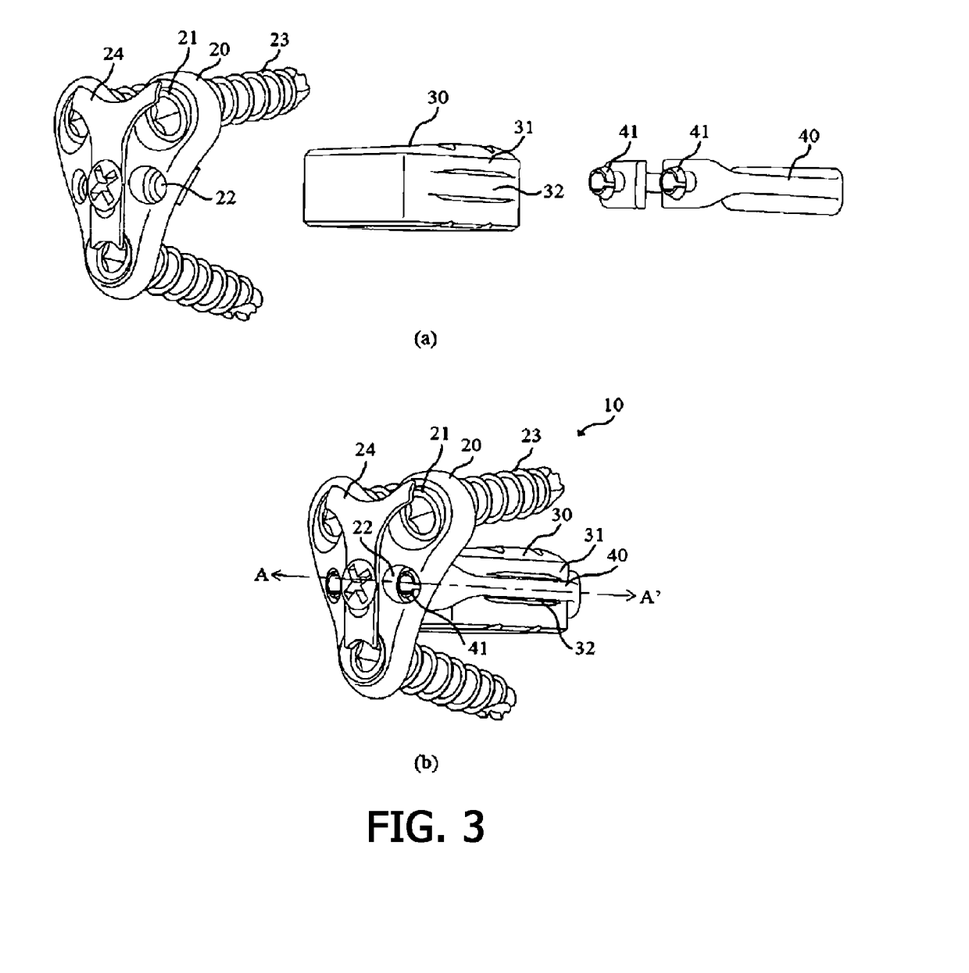
FIG. 3 is a view illustrating an example of a cervical spine fixation apparatus according to the disclosure.

FIG. 3 is a view illustrating an example of a cervical spine fixation apparatus according to the disclosure.

FIG. 3(a) is a perspective view illustrating a state in which a cervical spine fixation apparatus 10 according to the disclosure is separated into each component, and FIG. 3(b) is a perspective view illustrating a coupled state thereof.

The cervical spine fixation apparatus 10 according to the disclosure includes a body 20, a spacer 30, and a frame 40 located on lateral sides of the spacer 30, coupled to the spacer 30, and configured to include a coupling portion 41. The body 20 may include a screw hole 21, into which a screw 23 is inserted, and a hole 22, into which the coupling portion 41 is inserted. Also, a cover 24 may be included for preventing the screw 23 from being separated. The spacer 30 may be manufactured using a material such as a titanium alloy, polyether ether ketone (PEEK), and the like or may use a material extracted from a pelvic bone. Otherwise, crystallized glass ceramic may be used for manufacturing. However, when crystallized glass ceramic is used, the crystallized glass ceramic may be manufactured by mixing wollastonite ($CaSiO_3$), calcium hydroxyapatite ($Ca_{10}(PO_4)_6$), and akermanite ($Ca_2Mg(Si_2O_7)$) at an optimal ratio to have an adequate strength for being used as a spacer. Preferably, the crystallized glass ceramic may include each of $CaSiO_3$, $Ca_{10}(PO_4)_6$, and $Ca_2Mg(Si_2O_7)$ at a 30 to 40 percentage of weight. When the crystallized glass ceramic is used, it is simple to manufacture the most adequate spacer for a patient using a 3D printer. Also, the spacer 30 may include a groove 32 on a lateral side 31. The frame 40, like the body 20, may be manufactured through mechanical processing by computer numerical control (CNC), machining center (MCT), or the like using one or more of materials such as stainless steel 316L (SUS 316L), cobalt chrome alloy (Co-28Cr-6Mo), pure titanium, an alpha-beta titanium alloy such as Ti-6Al-4V or Ti-6Al-7Nb, and nitinol. Also, the frame 40 includes the coupling portion 41 inserted into the hole 22 of the body 20.

Figure 4:
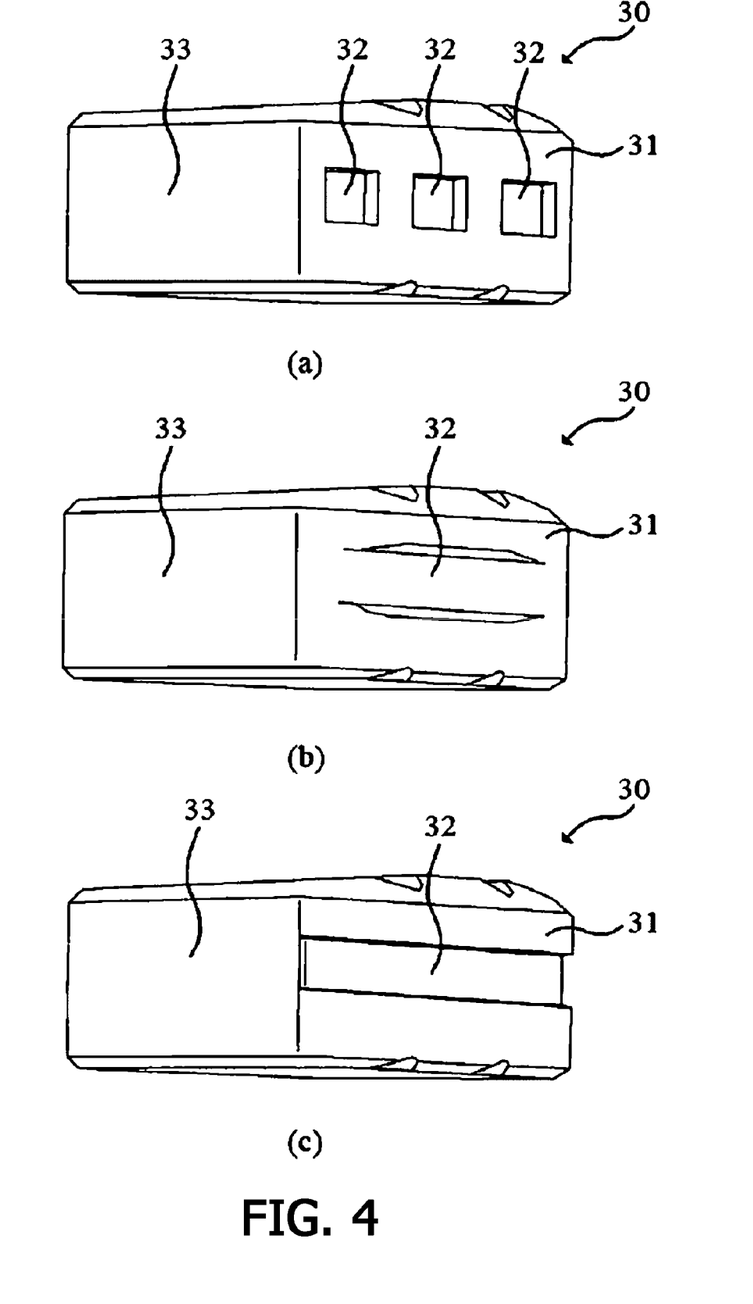
FIG. 4 is a view illustrating a variety of examples of a groove formed at a spacer according to the disclosure.

FIG. 4 is a view illustrating a variety of examples of the groove formed at the spacer according to the disclosure.

As shown in FIG. 4(*a*), a plurality of such grooves 32 may be formed on the lateral side 31 of the spacer 30. Otherwise, as shown in FIG. 4(*b*), one groove 32 may be formed lengthwise on the lateral side 31 of the spacer 30. Also, the shapes shown in FIGS. 4(*a*) and 4(*b*) may be formed on a part or the entirety of the lateral side 31 of the spacer 30. Also, as shown in FIG. 4(*c*), one groove 32 may be formed on the entirety of the lateral side 31 of the spacer 30. However, even when the grooves 32 having the shapes shown in FIGS. 4(*b*) and 4(*c*) are formed on the entirety of the lateral side 31 of the spacer 30, the groove may not be formed on the lateral side where the coupling portion 41 of the frame 40 is located. In the disclosure, when the spacer has a quadrangular shape as shown in FIG. 4, the spacer has four lateral sides 31 and 33. Although not shown in the drawings, those skilled in the art may understand fully that when the spacer has a circular shape, the spacer has one lateral side, and when the spacer has a polygonal shape, the number of lateral sides is determined according to the shape of the polygon.

Figure 5:
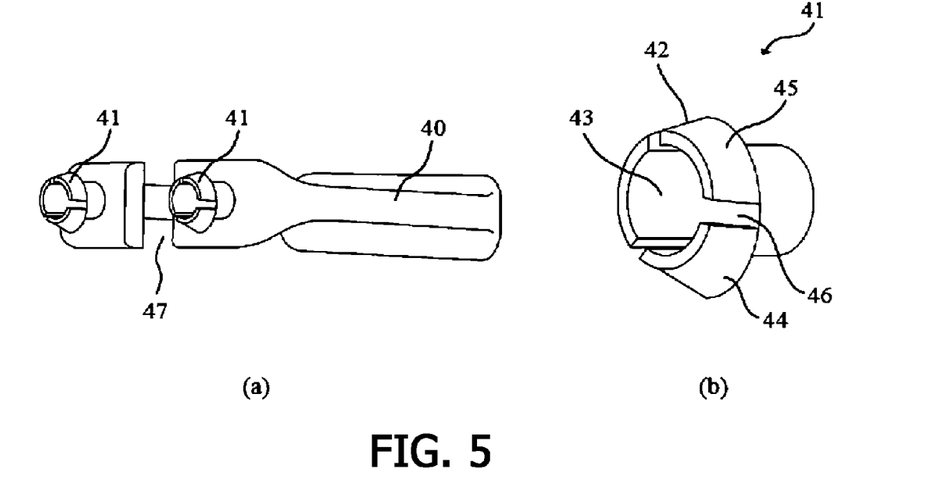
FIG. 5 is a view illustrating an example of a frame according to the disclosure.

FIG. 5 is a view illustrating an example of the frame according to the disclosure.

The frame 40 according to the disclosure includes the coupling portion 41. FIG. 4(*b*) is an enlarged view illustrating the coupling portion 41. Referring to FIG. 4(*b*), the coupling portion 41 includes a head 42. A lateral side 45 of the head 42 of the coupling portion 41 may incline such that a size of a top 43 of the head 42 is smaller than a size of a bottom 44 thereof. Also, the lateral side 45 of the head 42 may have a disconnection 46 to be easily deformed when being inserted into the hole 22 of the body 20. Also, when the frame 40 includes two coupling portions 41, a disconnection may be present at a side having shorter distance between the two coupling portions 41 when the spacer 30 is coupled to the frame 40.

Figure 6:
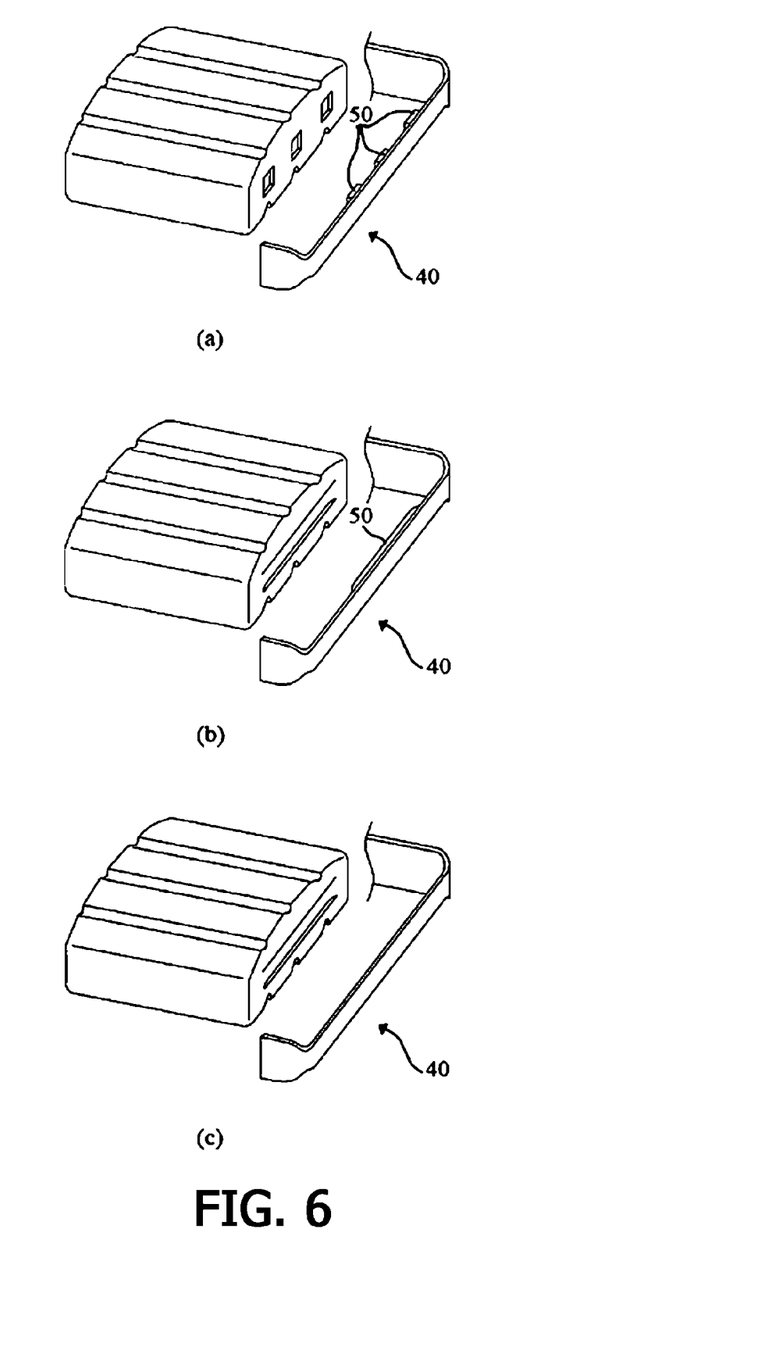
FIG. 6 is a view illustrating a variety of examples of coupling between a frame and the spacer according to the disclosure.

FIG. 6 is a view illustrating a variety of examples of coupling between the frame and the spacer according to the disclosure. For convenience of description, only the groove of the space which is coupled to the frame and a part of the frame which is coupled to the groove are illustrated.

As shown in FIG. 6(*a*), the frame 40 may include a protrusion 50 for coupling with the groove 32 of the spacer 30 shown in FIG. 4(*a*). Also, as shown in FIG. 6(*b*), the frame 40 may include the protrusion 50 for coupling with the groove 32 of the spacer 30 shown in FIG. 4(*b*). Also, as shown in FIG. 6(*c*), for coupling with the groove 32 of the spacer 30 shown in FIG. 4(*b*) or FIG. 4(*c*), the frame 40 may be inserted into the groove 32 without a protrusion such that the frame 40 may be coupled to the spacer 30. Also, notably, when the frame 40 is coupled to the groove 32 of the spacer 30, the frame 40 may protrude at or below 1 mm from the lateral side 31 of the spacer 30. This is because a possibility of touching nerves inside a cervical spine during a procedure is present in the case of protruding more than 1 mm. Accordingly, the groove 32 may be formed on the entirety of the lateral side 31 of the spacer 30. However, as described with reference to FIG. 4, the groove 32 may not be formed on the lateral side 33 of the spacer 30 in which the coupling portion 41 of the frame 40 is located.

Figure 7:
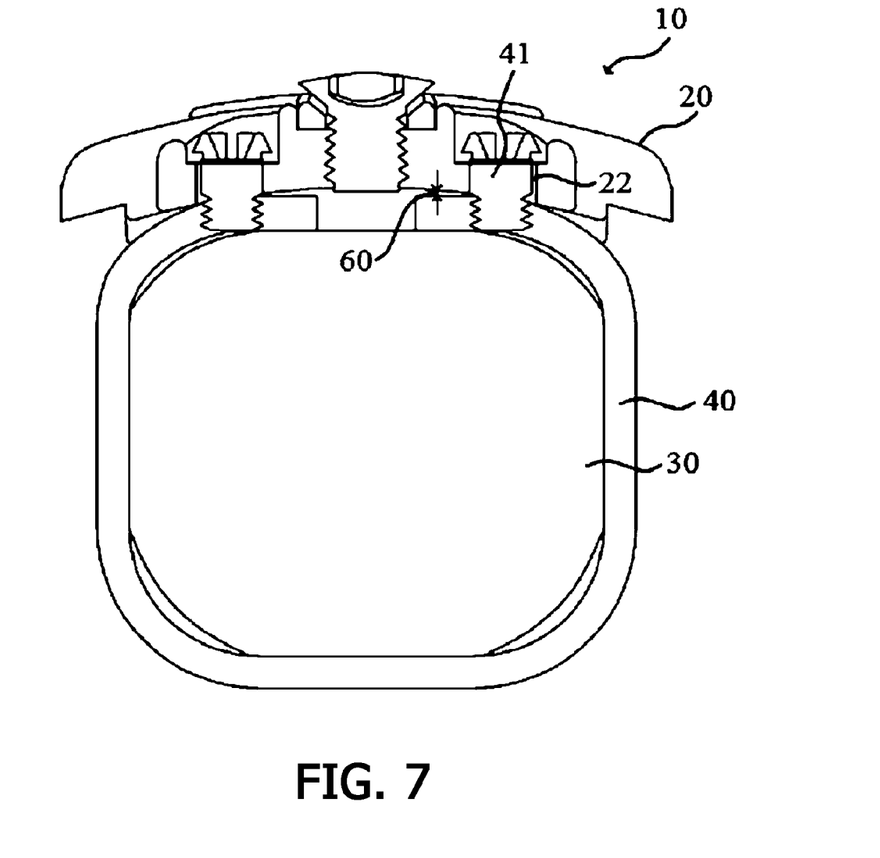
FIG. 7 is a cross-sectional view taken along line A-A' in FIG. 3.

FIG. 7 is a cross-sectional view taken along line A-A' in FIG. 3.

In the cervical spine fixation apparatus 10 according to the disclosure, the coupling portion 41 of the frame 40 is coupled to the hole 22 of the body 20 while the spacer 30 is coupled to the frame 40. When the frame 40 is coupled to the body 20, the frame 40 may be coupled to the body 20 with an interval 60 therebetween near the coupling portion 41. The interval 60 may be at or above 0.2 mm and less than 1.0 mm. The frame 40 may move and not be fixed to the body 20 due to the interval 60. When the interval 60 is less than 0.2 mm, the frame 40 is immovable from the body 20. When the interval 60 is more than 1.0 mm, the frame 40 may unintentionally move from the body 20 in another direction in addition to an upward direction or a downward direction of the body 20. A movement of the frame 40 about the body 20 will be described again with reference to FIG. 8. Although the coupling portion 41 may be integrated with the frame as a whole, the coupling portion 41 may be manufactured to have a screw shape and may be coupled to the frame 40 as shown in FIG. 7.

Figure 8:
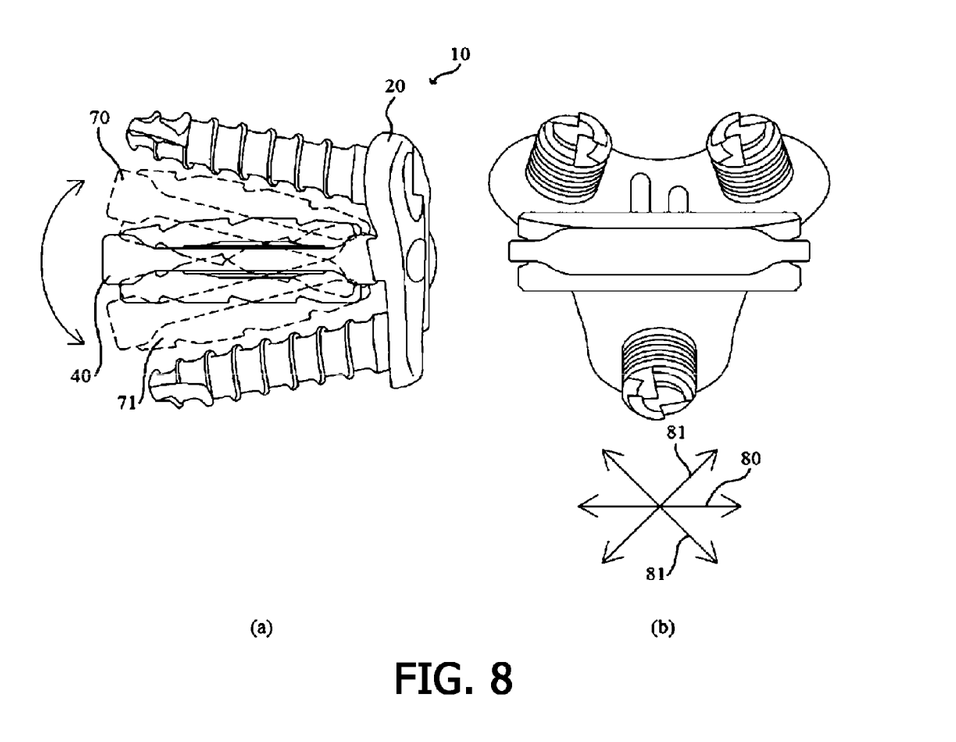
FIG. 8 is a view illustrating a movement of the frame in the cervical spine fixation apparatus according to the disclosure.

FIG. 8 is a view illustrating a movement of the frame in the cervical spine fixation apparatus according to the disclosure. FIG. 8(*a*) is a side view, and FIG. 8(*b*) is a bottom view.

In the cervical spine fixation apparatus 10 according to the disclosure, as shown in FIG. 8(*a*), the frame 40 coupled to the body 20 moves about the body while tilting in an upward direction 70 or a downward direction 71 of the body. The frame 40 which moves about the body while tilting in the upward direction 70 or the downward direction 71 is shown as dotted lines 70 and 71. Also, although the frame 40 moves while tilting in the upward direction or the downward direction of the body 20 as shown in FIG. 8(*a*) when the frame 40 includes two or more coupling portions 41, the frame 40 does not move freely in a rightward or leftward direction 80 or diagonal directions 81 shown as arrows in FIG. 8(*b*). However, when the interval 60 is greater than 1.0 mm as described with reference to FIG. 7, even when the two coupling portions 41 are present, the frame 40 may unintentionally move in various directions (the directions 80, 81, and the like). When the frame 40 moves in the various directions (80, 81, and the like), many variables occur and cause a difficulty in intervertebral fusion as well as an inconvenience to an operator.

Figure 9:
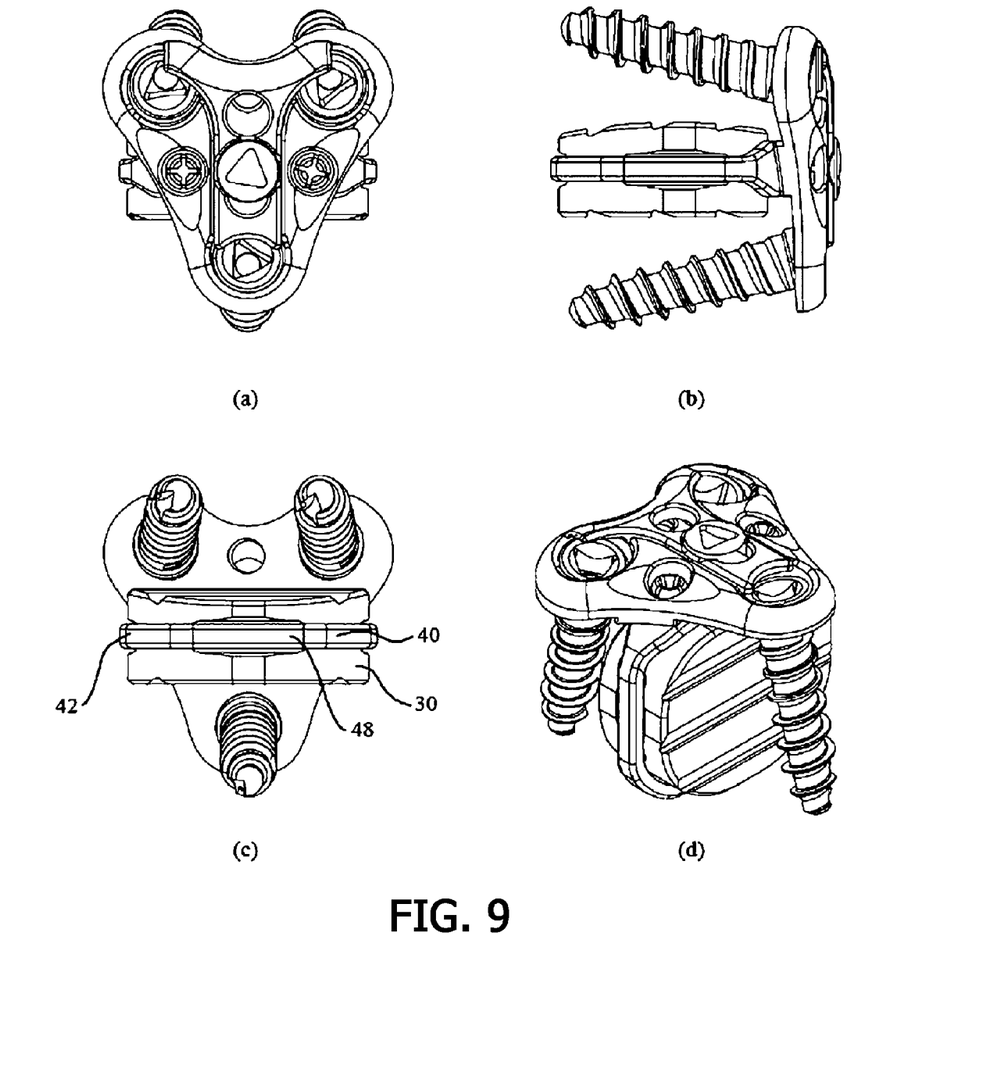
FIG. 9 is a view illustrating the cervical spine fixation apparatus in various directions according to the disclosure.

FIG. 9 is a view illustrating the cervical spine fixation apparatus in various directions according to the disclosure.

FIG. 9(*a*) is a plan view, FIG. 9(*b*) is a side view, FIG. 9(*c*) is a bottom view, and FIG. 9(*d*) is a perspective view. As shown in FIG. 9(*c*), a bottom surface 47 of the frame 40 may be formed to be wide so as to not show the groove formed on the lateral side of the spacer 30 when the spacer 30 is coupled to the frame 40.

Figure 10:
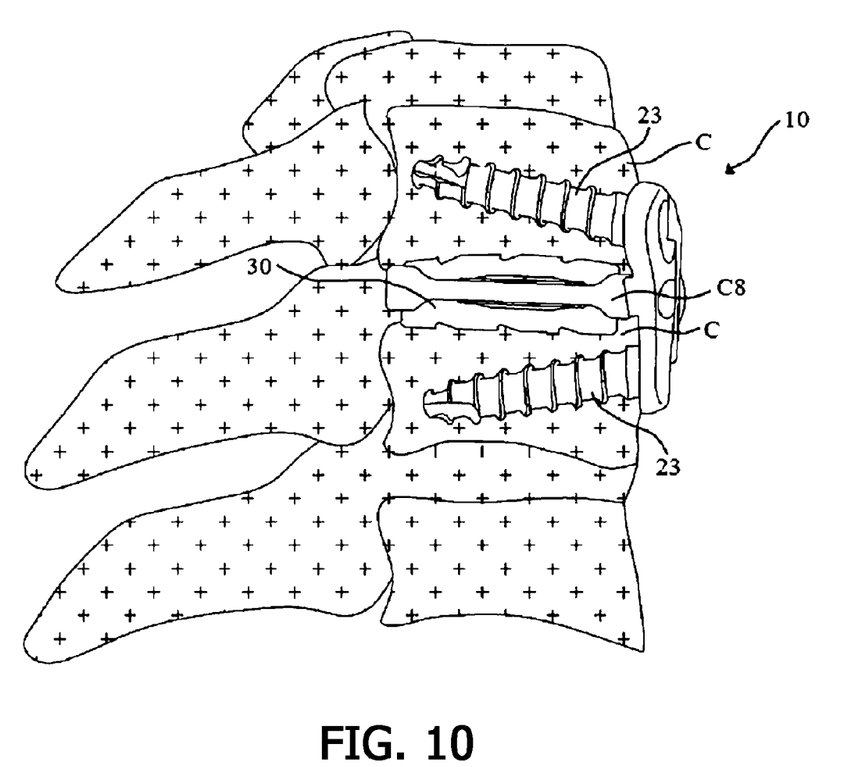
FIG. 10 is a view illustrating an example of the use of the cervical spine fixation apparatus according to the disclosure.

FIG. 10 is a view illustrating an example of the use of the cervical spine fixation apparatus according to the disclosure.

In the cervical spine fixation apparatus 10 according to the disclosure, the spacer 30 may be located between two bones C of the cervical spine, and the cervical spine fixation apparatus 10 may be used while being fixed to the bones C of the cervical spine by the screw 23.

Figure 11:
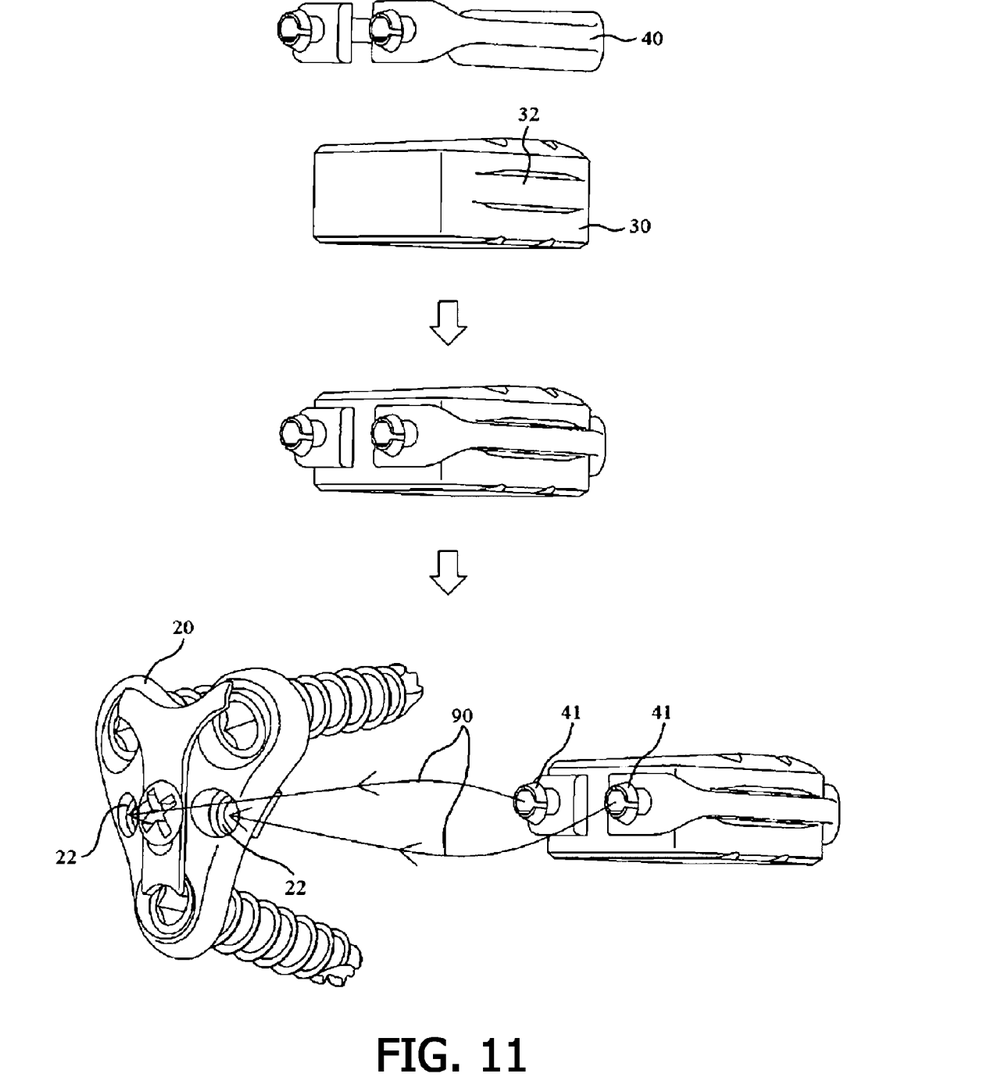
FIG. 11 is a view illustrating an example of assembly of the cervical spine fixation apparatus according to the disclosure.

FIG. 11 is a view illustrating an example of coupling of the cervical spine fixation apparatus according to the disclosure.

In the cervical spine fixation apparatus 10 according to the disclosure, the frame 40 and the spacer 30 are coupled using the groove 32 formed on the lateral side of the spacer 30. Afterwards, the head of the coupling portion 41 of the frame 40 is pushed in and coupled to the hole 22 of the body 20 in an arrow direction 90. As a result of being pushed and coupled in the arrow direction 90, a lateral side of the head of the coupling portion 41 may be disconnected as described above with reference to FIG. 5.

Figure 12:
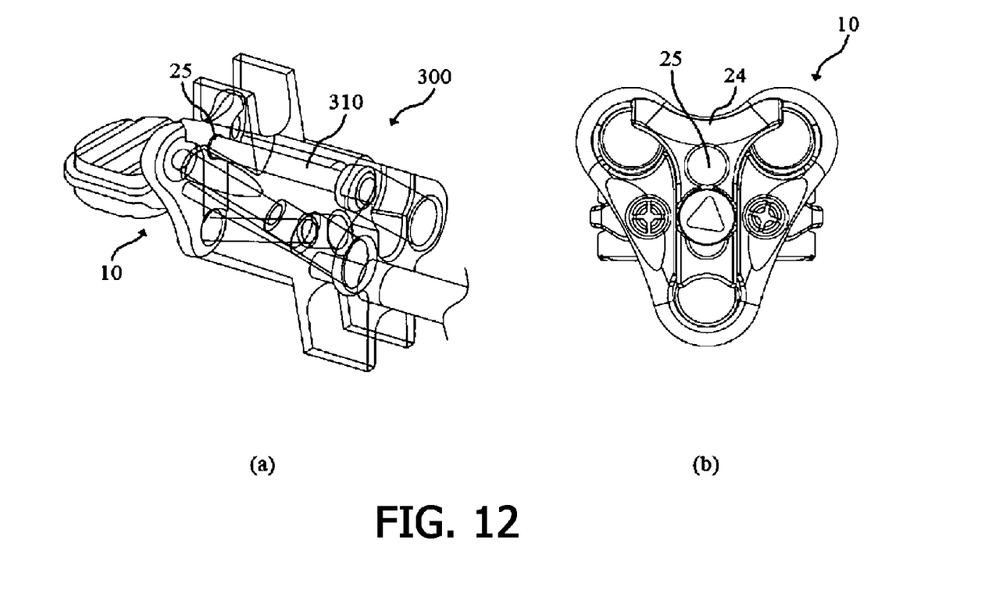
FIG. 12 is a view illustrating an example of the use of the cervical spine fixation apparatus according to the disclosure.

FIG. 12 is a view illustrating an example of the use of the cervical spine fixation apparatus according to the disclosure.

When the cervical spine fixation apparatus 10 according to the disclosure is used, a holder 300 may be connected to the cervical spine fixation apparatus 10 to use for convenience of the use. The cervical spine fixation apparatus 10 may include a hole 25 to which a link 310 configured to connect the holder 300 to the cervical spine fixation apparatus 10 is coupled. The hole 25 may be formed to be passing through the cover 24. FIG. 12(*a*) is a side view illustrating a state in which the cervical spine fixation apparatus 10 and the holder 300 are coupled, and FIG. 12(*b*) is a detailed plan view illustrating the hole 25 formed in the cervical spine fixation apparatus 10, which is coupled to the link 310 of the holder 300.

Figure 13:
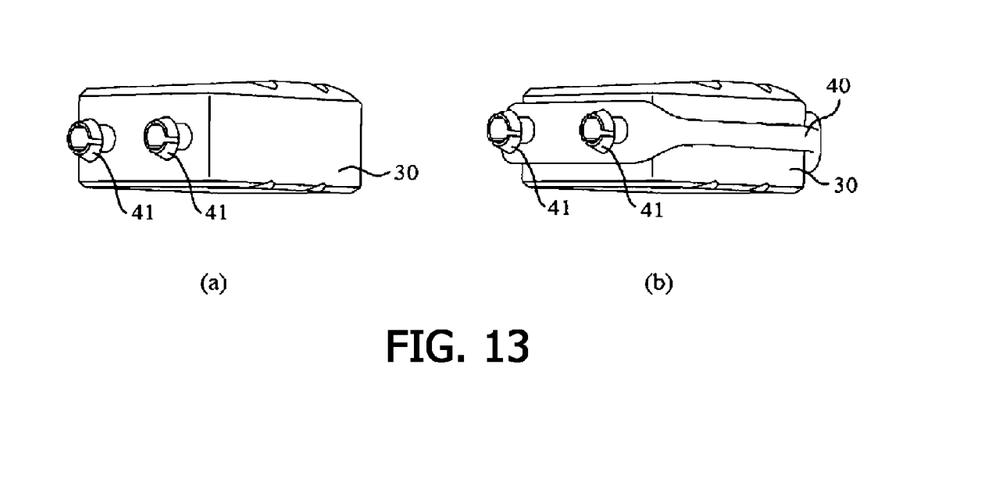
FIG. 13 is a view illustrating a variety of examples of the cervical spine fixation apparatus according to the disclosure.

FIG. 13 is a view illustrating a variety of examples of the cervical spine fixation apparatus according to the disclosure.

FIG. 13(*a*) illustrates that the spacer 30 includes the coupling portion 41. Since the coupling portion 41 is formed at the spacer 30 without a frame, a problem in which the frame described with reference to FIG. 6 protrudes from the lateral side of the spacer 30 does not occur. FIG. 13(*b*) illustrates that the frame 40 which includes the coupling portion 41 is not coupled to the spacer 30 through the groove 32 formed on the lateral side of the spacer 30 and is integrated with the spacer 30 as a whole. In a method in which the coupling portion 41 is formed on the spacer 30 or the frame 40, the coupling portion 41 may be provided while being integrated with the spacer 30 or the frame 40 as a whole, or the coupling portion 41 may be manufactured in the screw shape shown in FIG. 7 and then coupled to the spacer 30 or the frame 40.

Hereinafter, a variety of embodiments of the disclosure will be described.

(1) In a cervical spine fixation apparatus, the apparatus includes a body, a spacer, and a frame which is located on a lateral side of the spacer and coupled to the spacer and includes a coupling portion to be coupled to the body, in which the body includes a hole into which the coupling portion of the frame is inserted.

(2) In the cervical spine fixation apparatus, the spacer includes a groove formed on the lateral side thereof.

(3) In the cervical spine fixation apparatus, the groove is formed on the entire lateral side of the spacer.

(4) In the cervical spine fixation apparatus, a part of the frame is coupled to the groove formed on the spacer.

(5) In the cervical spine fixation apparatus, the frame includes a protrusion to be coupled to the groove.

(6) In the cervical spine fixation apparatus, there are two or more coupling portions.

(7) In the cervical spine fixation apparatus, there are two coupling portions.

(8) In the cervical spine fixation apparatus, the frame is not connected at a side having a shorter distance between the two coupling portions.

(9) In the cervical spine fixation apparatus, the coupling portion includes a head, and a lateral side of the head inclines such that a top of the head is smaller than a bottom thereof.

(10) In the cervical spine fixation apparatus, the lateral side of the head of the coupling portion is not connected in one or more spaces.

(11) In the cervical spine fixation apparatus, the body includes two holes, the spacer includes a groove on the lateral side thereof, the frame is coupled to the groove formed on the lateral side of the spacer and includes the two coupling portions, and the coupling portions are coupled to the holes and include heads, a lateral side of the head inclines such that a top thereof is smaller than a bottom thereof and is disconnected one or more times.

(12) In the cervical spine fixation apparatus, the frame moves about the body.

(13) In the cervical spine fixation apparatus, the body and the frame are spaced at an interval apart near the coupling portion.

(14) In the cervical spine fixation apparatus, the interval is 0.2 or more and less than 1.0 mm.

(15) In the cervical spine fixation apparatus, the frame moves while tilting in an upward or downward direction of the body.

(16) In the cervical spine fixation apparatus, the body includes the two holes, the spacer includes the groove on the lateral side thereof, the frame is coupled to the groove formed on the lateral side of the spacer and includes the two coupling portions, and the coupling portions are coupled to the holes of the body such that the body and the frame are spaced at an interval near the coupling portions.

(17) In the cervical spine fixation apparatus, when a holder to be coupled to the cervical spine fixation apparatus is used, the body includes a hole to be coupled to the holder.

(18) In a cervical spine fixation apparatus, the apparatus includes a body and a spacer including a coupling portion, in which the body includes a hole into which the coupling portion is inserted, and the spacer moves about the body.

(19) In the cervical spine fixation apparatus, the body and the spacer are spaced at an interval apart near the coupling portion.

(20) In the cervical spine fixation apparatus, the interval is 0.2 or more and less than 1.0 mm.

(21) In the cervical spine fixation apparatus, the spacer moves while tilting in an upward or downward direction of the body.

(22) In the cervical spine fixation apparatus, a frame integrated with the spacer as a whole is included, and the coupling portion is formed on the frame.

(23) In the cervical spine fixation apparatus, the body includes the two holes, the spacer includes the frame integrated with the spacer, the frame includes the two coupling portions formed thereon, and the coupling portions are coupled to the holes of the body such that the body and the frame are spaced at an interval near the coupling portions.

The invention claimed is:

1. A cervical spine fixation apparatus (10) comprising:
a body (20) including two holes;
a spacer (30) comprising a top portion, a bottom portion, two lateral sides; a front portion and a back portion; and
a frame (40) comprising a front portion including two coupling portions which are directly attached to and extend from said front portion, two lateral sides and a back portion, wherein said two lateral sides and said back portion of said frame (40) continuously surround said two lateral sides and said back portion of said spacer (30) and said frame (40) is coupled to the spacer (30), and said two coupling portions disposed in parallel insert into said two holes of said body to couple said frame (40) to the body (20),
wherein the frame (40) moves about the body,
wherein the frame (40) moves while tilting in an upward or downward direction relative to the body (20).

2. The cervical spine fixation apparatus of claim 1, wherein the spacer comprises a groove formed on one of said lateral sides thereof.

3. The cervical spine fixation apparatus of claim 2, wherein the groove is formed on the entire lateral side of the spacer.

4. The cervical spine fixation apparatus of claim 2, wherein a part of the frame is coupled to the groove formed on the spacer.

5. The cervical spine fixation apparatus of claim 4, wherein the frame comprises a protrusion to be coupled to the groove.

6. The cervical spine fixation apparatus of claim 1, wherein there are two or more coupling portions.

7. The cervical spine fixation apparatus of claim 6, wherein the frame is not connected at a side having a shorter distance between the two coupling portions.

8. The cervical spine fixation apparatus of claim 1, wherein each of the coupling portions comprises a head, and a lateral side of the head inclines such that a top of the head is smaller than a bottom thereof.

9. The cervical spine fixation apparatus of claim 8, wherein the lateral side of the head of the coupling portion is not connected in one or more spaces.

10. The cervical spine fixation apparatus of claim 1,
wherein the spacer comprises a groove on one of said lateral sides thereof,
wherein the frame is coupled to the groove formed on the one of said lateral sides of the spacer, and
wherein the two coupling portions are coupled to the holes and comprise a head, and a lateral side of the head inclines such that a top thereof is smaller than a bottom thereof and is disconnected one or more times.

11. The cervical spine fixation apparatus of claim 1, wherein the body and the frame are spaced apart at an interval near the coupling portion.

12. The cervical spine fixation apparatus of claim 11, wherein the interval is in a range between 0.2 mm to 1.0 mm.

13. The cervical spine fixation apparatus of claim 1,
wherein the spacer comprises a groove on the lateral sides thereof,
wherein the frame is coupled to the groove formed on the lateral sides of the spacer, and
wherein the coupling portions are coupled to the holes of the body such that the body and the frame are spaced at an interval near the coupling portions.

14. The cervical spine fixation apparatus of claim 1, wherein when a holder to be coupled to the cervical spine fixation apparatus is used, the body comprises a different hole to be coupled to the holder.

* * * * *